United States Patent [19]

Coffey et al.

[11] Patent Number: 4,876,747
[45] Date of Patent: Oct. 31, 1989

[54] GLOVE WITH EASY SAFE REMOVAL MEANS

[76] Inventors: Carl E. Coffey; Darlene M. Coffey, both of 8408 Garland Rd., Pasadena, Md. 21122

[21] Appl. No.: 190,076

[22] Filed: May 4, 1988

[51] Int. Cl.⁴ .............................................. A41D 19/00
[52] U.S. Cl. .............................................. 2/168; 2/169; 2/161 R; 223/111
[58] Field of Search ............... 2/161 R, 159, 160, 162, 2/168, DIG. 7, 164, 169, 158, 167; 223/111

[56] References Cited

U.S. PATENT DOCUMENTS

| | | | |
|---|---|---|---|
| 1,426,797 | 8/1922 | Wangelin | 2/160 |
| 1,507,707 | 9/1924 | Morganstern | 2/168 X |
| 2,041,254 | 5/1936 | Lipshutz | 2/160 |
| 3,515,320 | 6/1970 | Wintersberger | 223/111 |
| 4,696,065 | 9/1987 | Elenteny | 2/168 |

Primary Examiner—Peter Nerbun
Attorney, Agent, or Firm—Richard C. Litman

[57] ABSTRACT

An elastomeric glove with a raised loop attached to the wrist portion thereof allows for the easier removal of said glove and prevents the user from making physical contact with the external surface of the glove, particularly a concern when the exterior of the glove has become contaminated with a biological or chemical hazard or the like. A hook used in conjunction with each glove during the removal process makes it possible to easily and neatly remove both gloves simultaneously from the hands of the user—leaving each glove inverted for clean handling while said gloves are disposed of.

7 Claims, 2 Drawing Sheets

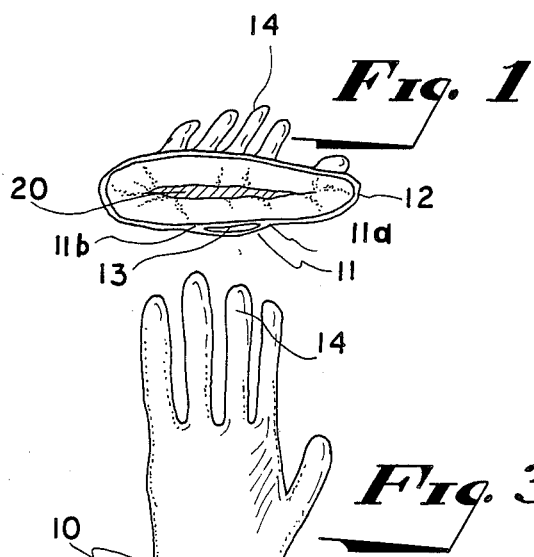
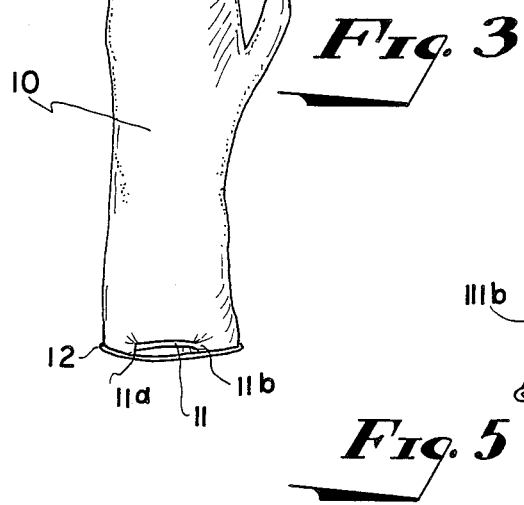
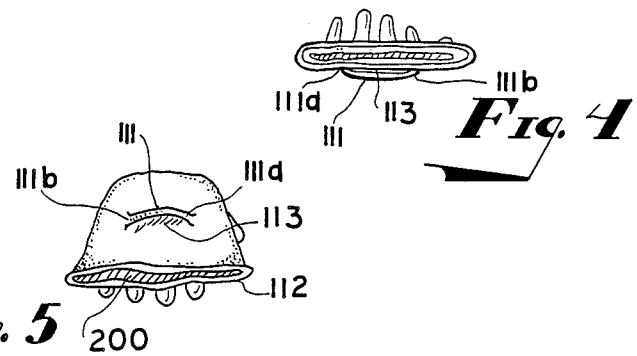
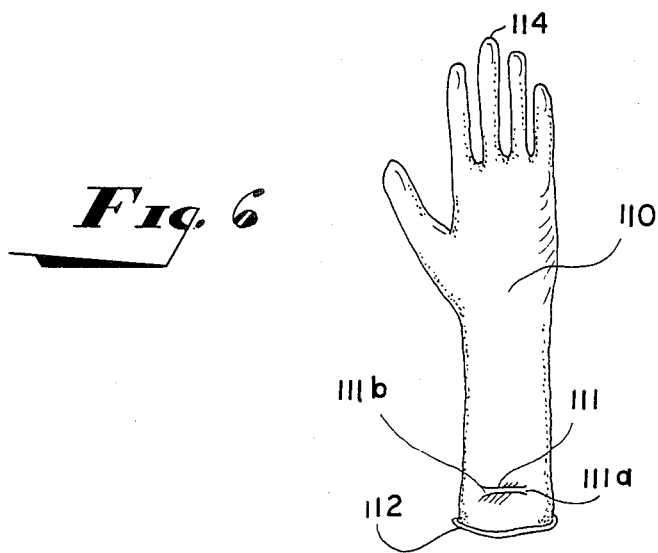

GLOVE WITH EASY SAFE REMOVAL MEANS

FIELD OF THE INVENTION

The present invention relates to elastomeric gloves, and more particularly the invention is directed to an improved elastomeric glove construction for providing facilitated and more sanitary removal of said gloves after they have been used.

BACKGROUND OF THE INVENTION

It has long been the practice in the health care profession to wear gloves for protective and sanitary purposes. Conventionally, the gloves worn by health care professionals during surgical procedures, and the like, are fabricated from a thin gauge elastomeric material, such as latex. These elastomeric gloves stretch to the shape of the human hand, providing a very close fit and allowing relatively unimpaired sense of feel—necessities for many procedures performed by health care professionals. due to the close fit requirements for this class of gloves, it is very difficult to don or remove them. There already exists extensive prior art disclosing methods of treating the gloves so that they are more easily put on the hands of the user, but there still exists a need for a means to more easily and neatly remove the gloves. With the gloves currently employed by health care professionals, it is necessary to reach under the edge of the opening at the wrist portion of the glove with one finger of the opposite hand and peel the edge down the wrist or forearm or the like towards the fingertips, thereby removing the gloves, reaching under the edge at the opening of the glove while it is worn and stretched taught is made difficult.

The matter of glove removal is further complicated when sanitation is a concern. During the many procedures where elastomeric gloves are used, the exterior surface may be contaminated with biological or chemical hazards or the like. Consequently, when it is necessary to reach under the edge at the opening of the glove at the wrist or forearm, the protection offered by the implementation of the gloves is diminished significantly since the exteriors of both gloves worn by the user represent a risk of contamination. In order to remove the first contaminated glove, the user must use the second contaminated glove to reach under the edge at the opening of the first glove, thereby risking physical contact with said contaminated exterior of said second glove.

Merely as an example, elastomeric gloves of the type previously referred to are conventionally worn during surgical procedures by the surgeon performing the procedure and the staff assisting the surgeon. In a large portion of surgical procedures commonly performed, it is inevitable that the exterior surface of the gloves worn by the surgeon become contaminated with the blood of the patient. Afterwards, should the surgeon try to remove the gloves from his hands by himself by reaching under the edge at the opening of one of the gloves with the second gloved hand, it is virtually impossible to escape making physical contact with the contaminated surface of the second glove. With the growing concern about blood transmittable diseases such as Acquired Immune Deficiency Syndrome, otherwise known as AIDS, contact with the blood of other persons, who may or may not be infected with such a virus, is very undesirable.

DESCRIPTION OF PRIOR ART

Various prior art gloves, and the like, as well as their apparatuses and the method of their construction in general, are known and are found to be exemplary of the U.S. prior art. They are:

| U.S. Pat. No. | Inventor |
|---|---|
| 1,507,707 | Morganstern |
| 4,696,065 | Elenteny |

1,507,707 discloses a Wash or Dish Cloth comprising a mitt-like construction with an elastic band around the opening at the wrist portion and a loop attached at the distal end where the fingertips are positioned. The device serves to keep the hand placed therein dry and clean while washing dishes. The loop allows the device to be removed from the hand therein by the opposite hand without contacting the wet or soiled surface of the mitt. When the loop is pulled on, the elastic band around the perimeter of the opening at the wrist portion is forced to expand and allows the mitt to slide off the hand. However, a loop fastened at the fingertip area of an elastic grove would not aid in the removal of the glove because of the frictional forces between the glove and the hand therein and because of the stretching of the elastomeric material from which the glove is manufactured.

In 4,696,065 Elenteny discloses Peel Away Multi-Layer Gloves. Although the present invention is not concerned with multiple layer gloves, one of the components of the glove is a tab located along the edge of the opening of the glove where the glove terminates at the wrist or forearm or the like. The tab is a small flat extension of the layer of the elastomeric material from which the glove is constructed. However, with the tab located on the edge of the glove at the opening at the wrist portion, the tab lies flat next to the skin. In order to grasp the tab it is necessary to bring the opposite contaminated glove into close proximity with the exposed skin beyond the edge of the glove, thereby risking contact between the contaminated second glove and said skin. Furthermore, since the tab must be grasped in order to be used, said tab constructon limits the possible ways to remove the glove of which it is part.

These patents or known prior uses teach and disclose various types of elastomeric gloves and glove removal devices of sorts and of various manufactures, and the like, as well as methods of their construction; but none of them, whether taken singly or in combination, disclose the specific details of the combination of the invention in such a way as to bear upon the claims of the present invention.

SUMMARY OF THE INVENTION

The present invention focuses on means to remove gloves constructed from an elastomeric material. It is an object, advantage, and feature of the present invention to provide a novel elastomeric glove that is equipped with a loop, providing means to facilitate the removal of the glove from the hand.

Another object of the present invention is directed further to a means of removing an elastomeric glove after its exterior surface has become contaminated by possibly hazardous substances, said means reducing the potential of any physical contact between the contaminated exterior surface and the body of the wearer.

In accordance with the preferred form of the invention, the glove is a neuter glove, in that the same glove shape is used for both hands. The glove is formed of very thin elastomeric materials such as latex rubber or the like, and a raised loop is formed on the wrist portion thereof by any suitable means such as, for example, by adhesive bonding or heat welding of a separate piece of material to the exterior surface of the glove or by forming the loop during the molding process of the glove manufacture.

The placement of the loop on the glove is such that, while the glove is being peeled off from the hand, the glove becomes inverted so as to contain the contaminated outer surface within the inverted glove structure. Furthermore, the loop may be attached or formed a suitable distance up from the edge of the opening of the glove so that it may be grasped by the opppsite hand without said opposite hand touching any skin. Consequently, should the opposite hand also be covered with a contaminated glove, the act of removing first glove will not cause the second contaminated glove to contact the skin of the first hand.

Otherwise, the loop may be located along the edge of the opening, and a hook may be used to assist in the removal of the gloves—either one glove at a time with one hook or both gloves simultaneously with two hooks. In addition, with this second structural configuration each glove becomes completely inverted when it is removed.

These, together with other objects and advantages of the invention reside in the details of the process and the operation thereof, as is more fully hereinafter described and claimed. References are made to drawings forming a part hereof, wherein like numerals refer to like parts throughout.

DESCRIPTION OF THE SEVERAL VIEWS OF THE DRAWING

FIG. 1 is an end view of the glove showing the opening thereof partially collapsed and the loop on the bottom edge of the opening;

FIG. 2 is an end view of the glove completely collapsed with the loop on the top;

FIG. 3 is a plan view of the glove showing the loop located at the edge of the opening of the glove;

FIG. 4 is another end view of the glove with the loop on the bottom and away from the edge of the opening of the glove;

FIG. 5 is a perspective view of the glove showing the glove folded over itself and showing the loop positioned away from the edge of the opening of the glove;

FIG. 6 is a plan view of the glove with the loop attached away from the edge of the opening of the glove;

DESCRIPTION OF THE PREFERRED EMBODIMENTS

Figure 7:
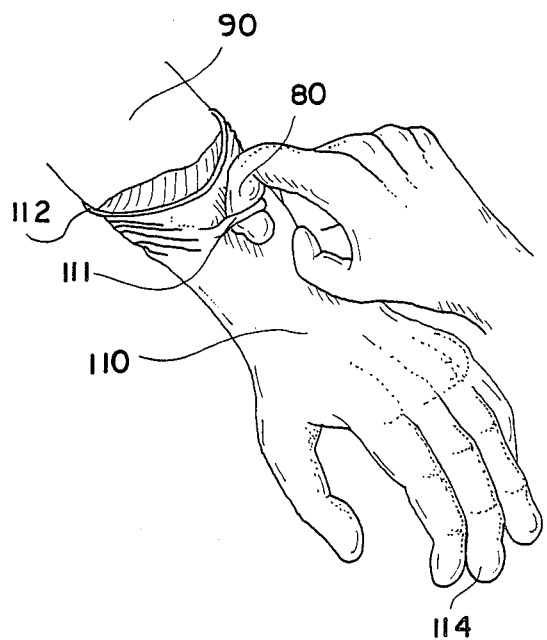
FIG. 7 is a perspective view of the glove in use, said glove with the loop attached away from the edge of the opening thereof, illustrating the use of the opposite gloved hand to remove the glove.

Referring now to the drawing there is shown in FIG. 3 a plan view of an embodiment of an elastomeric glove 10, which will be herein after referred to a the first embodiment, comprising a thin layer of an elastomeric material such as latex, which is formed so as to resemble the shape of a human hand and is adapted to be worn thereon. Said elastomeric glove 10 including a loop 11 secured adjacent to the edge 12 at the opening of the glove by heat welding, adhesive bonding, molding, cutting and extruding, or other similar means.

Now referring to the end view of the invention shown by FIG. 1, there is shown the opening 20 of the glove 10 which is partially collapsed and the and the loop 11 secured adjacent to the edge 12 of said opening; said loop 11 is of any suitable length which is longer than the distance between the tow points 11a and 11b where said loop connects with the exterior surface of the glove 10 so that the loop is bowed outwards, providing a clearance 13 between the exterior suface of the glove and the underside of the loop 11.

Figure 8:
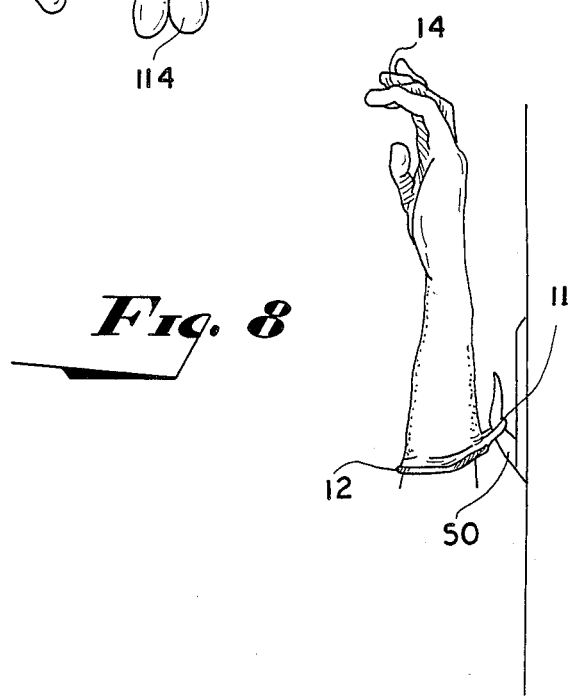
FIG. 8 is a perspective view of the glove in use, said glove with the loop attached at the edge of the opening thereof, illustrating the use of a hook to remove the glove.

FIG. 8 shows the first embodiment of the glove being removed with the assistance of a fixed hook 50. To remove the glove, the wearer of the glove maneuvers the loop 11 over and around the hook 50 so that said hook protrudes up through the clearance 13 defined by said loop and the exterior of said glove and engages the loop. With the hook engaging the loop, by bringing the hand inside the glove down past the hook from the proximal end at the edge 12 of the the opening of the glove towards the distal end at the fingertips 14, the glove is peeled back off of the hand and turned inside out. Since the loop of the first embodiment is located adjacent to the edge 12 of the opening, the glove is completely inverted during the process, thus enclosing the entire exterior surface of the glove.

The loop allows the glove to be removed by using a fixed hook or the like as in the manner just hereinabove described; furthermore, since the present invention allows for the removal of an elastomeric glove without the use of the opposite hand, with two hooks or the like it is possible to remove a glove from both hands at the same time.

The improvements the present invention offers in maintaining sanitary conditions are as equally important as the ease of glove removal provided. By using the method of removal above-referenced in connection with the first embodiment, having a loop adjacent to the edge of the opening of the glove and implementing a fixed hook or the like, it is:

(1) unnecessary to bring the possibly hazardous contaminated exterior surface of the glove on the opposite hand into close proximty with any exposed flesh; and (2) safer and cleaner to handle the completely inverted glove since the contaminated exterior surface is completely contained therewithin.

Now with reference to FIG. 6, there is shown a second embodiment of the present invention, to be referred to as such hereinafter. The second embodiment is substantailly identical to the first embodiment except that the loop 111 is secured at a suitable distance from the edge 112 of the opening of the glove 110 so that said loop may be grasped by the opposite hand without any significant likelihood of the opposite hand contacting the flesh exposed beyond the edge 112 of the glove 110. Consequently, should the opposite hand be covered with a similar glove and the exterior of this glove also be contaminated with a potentially hazardous substance, the risk of the contaminated exterior of the glove on the opposite hand coming into contact with the exposed flesh beyond the edge 112 of the glove being removed is substantially reduced, if not entirely eliminated.

FIG. 5 shows the glove of the second embodiment folded over upon itself with the opening 200 at the end of the glove and the clearance 113 defined by the space between the raised arcuate loop 111 and the exterior of the glove 110 being discernible. In the interest of clarity, FIG. 4 shows an end view of the second embodiment of the present invention more clearly displaying the clearance 113 defined by the raised loop 111 and the exterior surface of the glove between the points 111a and 111b where said loop connects to said glove.

As with the first embodiment, the elastomeric glove of the second embodiment also is inverted during the removal process, although only the portion of the glove between the loop 111 and the fingertips 114 is inverted. This is demonstrated in FIG. 7 where the elastomeric glove of the second embodiment is being removed by the opposite hand likewise clad in a similar glove. The index finger of the opposite glove 80 is inserted into the clearance defined by the loop 111 and the exterior of the glove 110, thereby engaging the loop so that as the loop is pulled down towards the fingertips 114, the glove 110 is peeled down off the hand and turned inside out from where the loop is located down to the fingertips. Said loop 111 is located far enough away from the edge 112 of the glove so that the opposite glove covering the index finger 80 does not contact the exposed flesh 90 beyond the edge 112 of the glove 110.

With both embodiments the glove may be formed by prefereably using a neuter type glove mold—a form resembling the configuration of a human hand. In one method of manufacture, said glove mold is suspended above a container of molten elastomeric material. Such material may any suitable rubber like formulation capable of producing a thin elastomeric layer and well known to those skilled in the art. After the mold has been coated with a suitable release agent to prevent the elastomeric material from bonding thereto, it is lowered into the container of liquid or molten elastomeric material so that the level thereof is below the upper edge of the mold. Following a short period of time within the molten material, the mold is withdrawn upwardly and is allowed to dry, a process that may take only a matter of seconds. A separate piece of material is then attached to the glove, whether still not cured or whether dried. This may be accomplished by adhesive bonding, or if suitable, by heat welding.

Another way to form the loop would be to temporarily attach a separate loop form to the mold prior to lowering it into the molten or liquid elastomeric material; thus, when the elastomeric is cured, the loop form which is enveloped by the elastomeric maiteral becomes part of the glove after it is removed from the glove mold.

In either course of manufacture, once the glove is dry, it is stripped from the mold using air jets, brushes, or any suitable means. Thereafter, a drying and friction reducing powder may be inserted on the inside of the glove to insure comfort of use and ease of putting on the glove.

The foregoing is considered as illustrative only of the principles of the invention. Further, since numerous modifications, and changes will readily occur to those skilled in the art, it is not desired to limit the invention to the exact construction and operation shown and described, and accordingly, all suitable modifications, and equivalents which may be resorted to, fall within the scope of the invention.

What is claimed is:

1. A surgical glove adapted to be worn on the human hand for protection against or deterring the transmission of, chemical or biological contamination, comprising;
    a unitary glove body of impervious elastomeric material having palm and back portions terminating in a wrist portion providing an opening extending substantially transversely of the length of the glove,
    removal means on the exterior of said back portion of said wrist portion adjacent to said opening,
    said removal means including an elongated loop member having distal portions and an intermediate portion, and
    said loop member distal portions affixed relative said glove back portion with said elongated loop member disposed substantially parallel to said opening and said loop member intermediate portion substantially spaced from said back portion to define an open unobstructed clearance therebetween when said elastomeric glove is being worn, whereby
    transmission of contamination on the exterior of the glove is deterred upon removal of the glove as a user employs a hook member within said loop member open clearance to engage said loop member intermediate portion to remove the glove from the hand by pulling it, in an inverted manner, back upon itself, beginning at said wrist portion opening.

2. The surgical glove as described in claim 1 wherein said loop is a separate piece of material attached to said glove by adhesive bonding means.

3. The surgical glove as described in claim 1 wherein said loop is a separate piece of material heat welded to said glove.

4. The surgical glove as described in claim 1 wherein said loop is formed from the layer of elastomeric material forming the glove by making two parallel incisions close together at the wrist portion.

5. The surgical glove as described in claim 1 wherein said loop is formed during the molding process during the manufacture of said glove.

6. The surgical glove as described in claim 5 wherein said loop member is molded with the glove by attaching a separate loop form to the glove mold whereby said separate loop form remains attached to the glove upon removal of the glove from the glove mold.

7. A system for providing increased protection against contamination following procedures wherein biological or chemical hazards exist, said system comprising:
    a surgical glove of molded elastomeric material having a back portion terminating in a wrist opening, an elongated loop member affixed to said glove back portion adjacent said wrist opening and parallel thereto, said loop member having an intermediate portion substantially spaced from said glove back portion to define an open unobstructed clearance therebetween when said glove is being worn;
    a stationary upwardly directed hook member adapted to engage within said glove loop member open clearance so that the glove may be removed from a user's hand by movement of the arm and hand past said hook member to cause the glove to be removed progressively from the hand in an inverted manner during the movement of the arm and hand past said hook member.

* * * * *